US010987368B2

(12) United States Patent
Vigsnæs et al.

(10) Patent No.: US 10,987,368 B2
(45) Date of Patent: *Apr. 27, 2021

(54) SYNTHETIC COMPOSITION FOR PREVENTING OR TREATING CVD

(71) Applicant: GLYCOM A/S, Hørsholm (DK)

(72) Inventors: Louise Kristine Vigsnæs, København (DK); Bruce McConnell, La Tour de Peilz (CH); Emma Elison, Hjärup (SE)

(73) Assignee: Glycom A/S, Hørsholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/183,431

(22) Filed: Jun. 15, 2016

(65) Prior Publication Data
US 2016/0287619 A1 Oct. 6, 2016

Related U.S. Application Data

(63) Continuation-in-part of application No. 15/104,794, filed as application No. PCT/DK2015/050385 on Dec. 8, 2015, now Pat. No. 10,828,313.

(30) Foreign Application Priority Data

Dec. 8, 2014 (DK) .................................. 2014 70768

(51) Int. Cl.
A61K 31/702 (2006.01)
A61K 35/745 (2015.01)
A61K 9/20 (2006.01)
A61K 9/48 (2006.01)
A23L 33/21 (2016.01)
A23L 33/135 (2016.01)
A61K 35/00 (2006.01)

(52) U.S. Cl.
CPC .......... A61K 31/702 (2013.01); A23L 33/135 (2016.08); A23L 33/21 (2016.08); A61K 9/2054 (2013.01); A61K 9/4841 (2013.01); A61K 35/745 (2013.01); A23V 2002/00 (2013.01); A61K 2035/115 (2013.01)

(58) Field of Classification Search
CPC .. A61K 31/702; A61K 9/2054; A61K 9/4841; A61K 35/745; A61K 2035/115; A23L 33/21; A23L 33/135; A23V 2002/00
See application file for complete search history.

(56) References Cited

U.S. PATENT DOCUMENTS

| 4,895,838 | A | * | 1/1990 | McCluer | ................. | C07H 15/04 514/53 |
| 5,906,982 | A | * | 5/1999 | Prieto | .................... | A23C 9/203 514/61 |
| 10,828,313 | B2 | | 11/2020 | Salomonsson et al. | | |
| 10,835,544 | B2 | | 11/2020 | Vigsnaes et al. | | |
| 2011/0189149 | A1 | * | 8/2011 | Burcelin | ................. | A61K 35/74 424/93.45 |
| 2011/0256233 | A1 | | 10/2011 | Fournell et al. | | |
| 2012/0107838 | A1 | * | 5/2012 | Grainger | .......... | G01N 33/57415 435/7.23 |
| 2012/0171165 | A1 | | 7/2012 | Buck et al. | | |
| 2012/0208782 | A1 | * | 8/2012 | Frantz | ................. | A61K 31/7016 514/53 |
| 2012/0269891 | A1 | * | 10/2012 | McKearn | .............. | C07C 251/12 424/463 |
| 2012/0294840 | A1 | | 11/2012 | Newburg et al. | | |
| 2014/0037785 | A1 | | 2/2014 | Barboza et al. | | |
| 2015/0010670 | A1 | | 1/2015 | Mills et al. | | |

FOREIGN PATENT DOCUMENTS

| EP | 0691079 A2 | 10/1996 |
| EP | 1332759 | 8/2003 |
| EP | 2143341 | 1/2010 |
| EP | 2332552 | 6/2011 |
| WO | 98/43495 A1 | 10/1998 |
| WO | WO0104341 | 1/2001 |
| WO | 2007/073192 A2 | 6/2007 |
| WO | WO2007101862 | 9/2007 |
| WO | WO2009000803 | 12/2008 |
| WO | 2009/077352 A1 | 6/2009 |
| WO | 2009/082214 A1 | 7/2009 |
| WO | WO2010115934 | 10/2010 |
| WO | WO2010115935 | 10/2010 |
| WO | WO 2011100979 | 8/2011 |
| WO | WO2011100980 | 8/2011 |
| WO | 2011/119023 A1 | 9/2011 |
| WO | WO2011119033 | 9/2011 |
| WO | WO2012007588 | 1/2012 |
| WO | WO2012076323 | 6/2012 |
| WO | WO2012092153 | 7/2012 |

(Continued)

OTHER PUBLICATIONS

Rosmond, R et al. The hypothalamic-pituitary-adrenal axis activity as a predictor of cardiovascular disease, type 2 diabetes and stroke. Journal of Internal Medicine. 2000. 247: 188-197. (Year: 2000).*
Silvennoinen, R et al. Acute psychological stress accelerates reverse cholesterol transport via corticosterone-dependent inhibition of intestinal cholesterol absorption. Circulation Stress. 2012. 111(11): 1459-1469. (Year: 2012).*
Deveza, L et al. Therapeutic angiogenesis for treating cardiovascular diseases. Theranostics. 2012. 2(8): 801-814. (Year: 2012).*
Kenchaiah, S et al. Obesity and the risk of heart failure. The New England Journal of Medicine. 2002. 347(5): 305-313. (Year: 2002).*
Tanne, D et al. Body fat distribution and long-term risk of stroke mortality. Stroke. 2005. 36(5): 1021-1025. (Year: 2005).*

(Continued)

Primary Examiner — Renee Claytor
Assistant Examiner — Susan E. Fernandez
(74) Attorney, Agent, or Firm — Kunzler Bean & Adamson

(57) ABSTRACT

The invention relates to HMOs and compositions comprising thereof for reducing the risk of, preventing, or treating CVD and/or CDV associated pathological conditions or diseases in humans, particularly in overweight and obese humans.

15 Claims, No Drawings

(56) References Cited

FOREIGN PATENT DOCUMENTS

| WO | WO2012107865 | 8/2012 |
| --- | --- | --- |
| WO | WO2012113404 | 8/2012 |
| WO | WO2012113405 | 8/2012 |
| WO | WO2012127410 | 9/2012 |
| WO | WO2012155916 | 11/2012 |
| WO | WO2012156897 | 11/2012 |
| WO | WO2012156898 | 11/2012 |
| WO | WO2012158517 | 11/2012 |
| WO | WO2013036104 | 3/2013 |
| WO | 2013/057061 A1 | 4/2013 |
| WO | WO2013044928 | 4/2013 |
| WO | WO2013057061 | 4/2013 |
| WO | WO2013091660 | 6/2013 |
| WO | WO2013139344 | 9/2013 |
| WO | WO2013154725 | 10/2013 |
| WO | 2014/043330 A1 | 3/2014 |
| WO | WO2014164882 | 10/2014 |
| WO | 2014/187464 A1 | 11/2014 |
| WO | WO2014187464 | 11/2014 |
| WO | WO2015071401 | 5/2015 |
| WO | WO2015071402 | 5/2015 |
| WO | WO2015071403 | 5/2015 |
| WO | 2015/164021 A1 | 10/2015 |
| WO | 2016/091265 A1 | 6/2016 |
| WO | 2017/129639 A1 | 8/2017 |
| WO | 2017/129641 A1 | 8/2017 |
| WO | 2017/129648 A1 | 8/2017 |
| WO | 2017/129650 A1 | 8/2017 |

OTHER PUBLICATIONS

U.S. Appl. No. 15/183,404, Office Action Summary, dated Feb. 24, 2017.
U.S. Appl. No. 15/183,391, Office Action Summary, dated Feb. 24, 2017.
U.S. Appl. No. 15/183,391, Final Office Action Summary, dated Sep. 11, 2017.
Anatolltou, "Human Milk Benefits and Breastfeeding", Journal of Pediatric and Neonatoal Individualized Medicine, 2012; 1(1), pp. 11-18.
Asanuma et al., "Variation of Major Neutral Oligosaccharides Levels in Human Colostrum", European Journal of Clinical Nutrition, Apr. 2008, vol. 62, No. 4, pp. 488-494.
Burcelin, R. et al, "The gut microbiota ecology: a new opportunity for the treatment of metabolic diseases?", Frontiers in Bioscience, vol. 14, pp. 5107-5117, (Jun. 2009).
Backhed, F. et al, "The gut microbiota as an environmental factor that regulates fat storage", PNAS, 101:44:15718-15723, (Nov. 2, 2004).
Qin, J. et al, "A metagenome-wide association study of gut microbiota in type 2 diabetes", Nature, vol. 490, 55-60, (Oct. 2012).
Ley, R. et al, "Microbial ecology: human gut microbes associated with obesity", Nature, vol. 444, pp. 1022-1023, (Dec. 2006).
Tremaroli, V. et al, "Functional interactions between the gut microbiota and host metabolism", Nature, 489:7415:242-249, (Sep. 2012)).
Cani, P. et al, "Changes in gut microbiota control inflammation in obese mice through a mechanism involving GLP-2-driven improvement of gut permeability", Gut, vol. 58, pp. 1091-1103, (2009).
Kootte, R. et al, "The therapeutic potential of manipulating gut microbiota in obesity and type 2 diabetes mellitus", Diabetes, Obesity & Metabolism, vol. 14, pp. 112-120, (2012).
Turnbaugh, P. et al, "An obesity-associated gut microbiome with increased capacity for energy harvest", Nature, vol. 444, pp. 1027-1031, (Dec. 2006)).
Cani, P. et al, "Changes in gut microbiota control metabolic endotoxemia-induced inflammation in high-fat diet-induced obesity and diabetes in mice", Diabetes, vol. 57, pp. 1470-1481, (Jun. 2008).
Cani, P, et al, "Involvement of endogenous glucagon-like peptide-1(7-36) amide on glycaemia-lowering effect of oligofructose in streptozotocin-treated rats", J. of Endocrinology, vol. 185, pp. 457-465, (2005).
Cani, P. et al, "Metabolic endotoxemia initiates obesity and insulin resistance", Diabetes, vol. 56, pp. 1761-1772, (Jul. 2007).
Fearnley, G. et al, "Reduction of blood fibrinolytic activity in diabetes mellitus by insulin", The Lancet, 2(7111):1067, doi:10.1016/S0140-6736(59)91534-X, (Dec. 1959).
Ogston, D. et al, "Fibrinolysis in obesity", The Lancet, 284(7371):1205-1207, (Dec. 5, 1964).
Hotamisligil, G. et al, "IRS-1-mediated inhibition of insulin receptor tyrosine kinase activity in a TNF-alpha-and obesity-induced insulin resistance", Science, 271(5249):665-670, (Feb. 2, 1996).
Uysal, K. et al, "Protection from obesity-induced insulin resistance in mice lacking TNF-alpha function", Nature, vol. 389, pp. 610-614, (Oct. 9, 1997).
Amar, J. et al, "Intestinal mucosal adherence and translocation of commensal bacteria at the early onset of type 2 diabetes: molecular mechanisms and probiotic treatment", EMBO Molecular Medicine, vol. 3, pp. 559-572, (2011).
Andersson, A. et al, "Comparative analysis of human gut microbiota by barcoded pyrosequencing", PlosOne, 3(7): e2836, (Jul. 2008).
IDF Diabetes Atlas, International Diabetes Federation, 6th edition.
Urashima, T. et al, "Milk oligosaccharides", Nova Biomedical Books, NY, (2011).
Bezirtzoglou, E. et al, "Microbiota profile in feces of breast-and-formula-fed newborns by using fluorescence in situ hybridization", Anaerobe, vol. 17, pp. 478-482, (2011).
Bottacini, F. et al, "Diversity, ecology and intestinal function of bifidobacteria", Microbial Cell Factories, vol. 13, Suppl. 1, pp. S4, (2014).
Boulange, C. et al, "Impact of the gut microbiota on inflammation, obesity, and metabolic disease", Genome Medicine, 8:42, (2016).
Bridger, T., "Childhood obesity and cardiovascular disease", Paediatr. Child Health, 14(3):177-182, (2009).
Bruggencate, S. et al, "Functional role and mechanisms of sialyl-lactose and other sialyated milk oligosaccharides", Nutrition Reviews, 72(6):377-389, (2014).
Cani, P. et al, "Gut microbiota fermentation of prebiotics increases satietogenic and incretin gut peptide production with consequences for appetite sensation and glucose response after a meal", American J. of Clinical Nutrition, vol. 90, pp. 1236-1243, (2009).
Cano, P. et al, "Bifidobacterium CECT 7765 improves metabolic and immunological alterations associated with obesity in high-fat diet-fed mice", Obesity, 21(11):2310-2321, (Nov. 2013).
Chakraborti, C., "New-found link between microbiota and obesity", World J. of Gastrointestinal Pathophysiology, 6(4):110-119, (Nov. 2015).
Chichlowski, M. et al, "Bifidobacteria isolated from infants and cultured on human milk oligosaccharides affect intestinal epitherial function", J. Pediatr. Gastroenterol Nutrition, 55(3):321-327, (Sep. 2012).
Conterno, L. et al, "Obesity and the gut microbiota: does up-regulating colonic fermentation protect against obesity and metabolic disease?", Genes Nutrition, 6:241-260, (2011).
Nuckols, C., "The diagnostic and statistical manual of mental disorders, fifth edition (DSM-5)", American Psychiatric Association, 5th edition, (2013).
Dinan, T. et al, "Psychobiotics: A novel class of psychotropic", Biol. Psychiatry, 74:720-726, (2013).
Ferrari, A. et al, "Burden of depressive disorders by country, sex, age, and year: Findings from the global burden of disease study 2010", PLOS Medicine, 10(11):e1001547, (Nov. 2013).
Fukuda, S. et al, "Bifidobacteria can protect from enteropathogenic infection through production of acetate", Nature, vol. 469, pp. 543-549, (Jan. 2011).
Gabrielli, O. et al, "Preterm milk oligosaccharides during the first month of lactation", Pediatrics, vol. 128, pp. e1520-e1531, (Nov. 2011).
Gill, S. et al, "Metagenomic analysis of the human distal gut microbiome", Science, 312(5778):1355-1359, (Jun. 2006).
Jokela, M. et al, "Association of metabolically healthy obesity with depressive symptoms: pooled analysis of eight studies", Molecular Psychiatry, vol. 19, pp. 1-5, (2013).

(56) References Cited

OTHER PUBLICATIONS

Kendler, K. et al, "Illicit psychoactive substance use, abuse and dependence in a population-based sample of Norwegian twins", Psychol. Med., 36(7):955-962, (Jul. 2006).
Matthan, N. et al, "Sex-specific differences in predictive value of cholesterol homeostasis markers and 10-year cardiovascular disease event rate in Framingham offspring study participants", J. American Heart Assn., vol. 2, pp. e005066-e005079,(2013).
Rolland-Cachera, M., "Childhood obesity: current definitions and recommendations for their use", Intl. J. of Pediatric Obesity, vol. 6, pp. 325-331, (2011).
Sanchez, M. et al, "Childhood obesity: A role for gut microbiota?", Intl. J. of Environ. Res. Public Health, vol. 12, pp. 162-175, (2015).
Savignac, H. et al, "Bifidobacteria exert strain-specific effects on stress-related behavior and physiology in BALB/c mice", Neurogastroenterology & Motility, vol. 26, pp. 1615-1627, (2014).
Schwiertz, A. et al, "Microbiota and SCFA in lean and overweight healthy subjects", Obesity, 18(1):190-195, (Jan. 2010).
Shah, M. et al, "Effects of GLP-1 on appetite and weight", Rev. Endocr. Metab. Disorder, 15(3):181-187, (Sep. 2014).
Tarr, A. et al, "The prebiotics 3'sialyllactose and 6'sialyllactose diminish stressor-induced anxiety-like behavior and colonic microbiota alterations: evidence for effects on the gut-brain axis", Brain Behav. Immun., vol. 15, pp. 181-215, (2015).
Verbeke, K. et al, "Towards microbial fermentation metabolites as markers for health benefits of prebiotics", Nutrition Research Reviews, vol. 28, pp. 42-66, (2015).
Walter, J. et al, "Detection and identification of gastrointestinal Lactobacillus species by using denaturing gradient gel electrophoresis and species-specific PCR primers", Appl. Environ. Microbiol., 66(1):297-303, (Jan. 2000).
Anonymous, "Obesity and overweight", WHO, Media Centre fact sheet, pp. 1-5, (Jan. 2015).
Zhang, C. et al, "Dietary modulation of gut microbiota contributes to alleviation of both genetic and simple obesity in children", EbioMedicine, vol. 2, pp. 966-982, (2015).
U.S. Appl. No. 15/183,404, Office Action Summary, dated Sep. 11, 2017.
PCT/DK2017/050198, "Notification of Transmittal of the International Search Report and the Written Opinion of the International Searching Authority, or the Declaration", dated Aug. 23, 2017, 20 pages.
Qin, J. et al, "A human gut microbial gene catalogue established by metagenomic sequencing", Nature, vol. 464, pp. 59-65, (2010).
Ettinger, G. et al, "The influence of the human microbiome and probiotics on cardiovascular health", Gut Microbes, 5:6:719-728, (2014).
Duranti, S. et al, "Exploration of the genomic diversity and core genome of the bifidobacterium adolescentis phylogenetic group by means of a polyphasic approach", Applied and Environmental Microbiology, 79(1):336-346, (Jan. 2013).
David A. Fields et al., "A Narrative Review of the Associations Between Six Bioactive Components in Breast Milk and Infant Adiposity", Obesity, vol. 24 | No. 6 | Jun. 2016, pp. 1213-1221.
Stanley IP et al., "Breastfeeding and Maternal and Infant Health Outcomes in Developed Countries", AHRQ Publication No. 07-E007, Apr. 2007, pp. 1-415.
USPTO, "Office Action Summary", U.S. Appl. No. 15/104,794, filed Dec. 20, 2018, pp. 1-23.
U.S. Appl. No. 15/183,391, Office Action Summary, dated Mar. 26, 2018.
U.S. Appl. No. 15/183,404, Office Action Summary, dated Mar. 26, 2018.
U.S. Appl. No. 15/183,456, Office Action Summary, dated Jan. 26, 2018.
Kresser, "A Healthy Gut Is the Key to Weight Loss", https://chriskresser.com/a-healthy-gut-is-the-hidden-key-to-weight-loss/, Oct. 29, 2010, pp. 1-3.
L. Lykouras et al., "Anxiety Disorders and Obesity", Psychiatriki, Oct.-Dec. 2011; 22(4):307-13, (abstract) p. 1.

U.S. Appl. No. 15/104,794, Office Action Summary, dated May 31, 2018.
U.S. Appl. No. 15/183,456, Office Action Summary, dated Sep. 10, 2018.
U.S. Appl. No. 15/183,404, Office Action Summary, dated Oct. 19, 2018.
U.S. Appl. No. 15/183,391, Office Action Summary, dated Oct. 16, 2018.
O.A. Alhaj et al., "Hypocholesterolaemic effect of Bifidobacterium animalis subsp. lactis (Bb12) and trypsin casein hydrolysate", Food Chemistry, journal homepage: www.elseviercom/locate/foodchem. Apr. 26, 2010, pp. 430-435.
S. Asakuma et al., "Physiology of Consumption of Human Milk Oligosaccharides by Infant Gut-associated Bifidobacteria", The Journal of Biological Chemistry vol. 286, No. 40, Oct. 7, 2011, pp. 34583-34592.
V. Bunesova et al., "Fucosyllactose and L-fucose utilization of infant Bifidobacterium longum and Bifidobacterium kashiwanohense", Bunesova et al. BMC Microbiology, DOI 10.1186/s12866-016-0867-4, Oct. 26, 2016, pp. 1-12.
CN Larsen et al., "Dose—response study of probiotic bacteria Bifidobacterium animalis subsp lactis BB-12 and Lactobacillus paracasei subsp paracasei CRL-341 in healthy young adults", European Journal of Clinical Nutrition. May 24, 2006, pp. 1284-1293.
Y. Lee et al., "Effects of Bifidobacterium animalis subsp. lactis BB-12® on the lipid/lipoprotein profile and short chain fatty acids in healthy young adults: a randomized controlled trial", Nutrition Journal, DOI 10.1186/s12937-017-0261-6, Jun. 29, 2017, p. 1-9.
M.L. Ritchie et al., "A Meta-Analysis of Probiotic Efficacy for Gastrointestinal Diseases", PLoS ONE 7(4): e34938. doi:10.1371/journal.pone.0034938, Apr. 18, 2012, pp. 1-11.
U.S. Appl. No. 15/104,794, Office Action Summary, dated Aug. 22, 2019, pp. 1-60.
U.S. Appl. No. 15/183,404, Office Action Summary, dated Aug. 2, pp. 1-29.
Barile et al.,"Human milk and related oligosaccharides as prebiotics", Current Opinion in Biotechnology, 2013, pp. 1-6, sciencedirect.com.
Druart et al., "Modulation of the Gut Microbiota by Nutrients with Prebiotic and Probiotic Properties", Proceedings of the IUNS 20th International Congress of Nutrition (Part 2), 2014, pp. 1-10, American Society for Nutrition.
U.S. Appl. No. 15/183,391, Office Action Summary, dated Jun. 14, 2019, pp. 1-35.
E. Elison et al., "Oral supplementation of healthy adults with 2!-O-fucosyllactose and lacto-N-neotetraose is well tolerated and shifts the intestinal microbiota", British Journal of Nutrition, Aug. 22, 2016, pp. 1-13.
G. Gibson et al., "The International Scientific Association for Probiotics and Prebiotics (ISAPP) consensus statement on the definition and scope of prebiotics", Nature Reviews | Gastroenterology & Hepatology, vol. 14, Aug. 2017, pp. 491-502.
U.S. Appl. No. 15/183,404, Office Action Summary, dated Mar. 20, 2020, pp. 1-52.
P.J. Whorewll et al, "Ethccy of an Encasulated Probiotic Bifidobacterium infantis 35624 in Woman with Irritable Bowel Syndrome", American Journal of Gastroenterology, 2006, pp. 1581-1590.
U.S. Appl. No. 15/104,794, Office Action Summary, dated Mar. 6, 2020, pp. 1-52.
U.S. Appl. No. 15/183,391, Office Action Summary, dated Feb. 19, 2020, pp. 1-30.
J. Chen et al., "Bifidobacterium adolescentis supplementation ameliorates visceral fat accumulation and insulin sensitivity in an experimental model of the metabolic syndrome", British Journal of Nutrition Sep. 14, 2011, 107, 1429-1434.
M. Joossens et al., "Dysbiosis of the faecal microbiota in patients with Crohn's disease and their unaffected relatives", Downloaded from gut.bmj.com on Aug. 22, 2011, pp. 631-637.
D. Guyonne et al. "Effect of a fermented milk containing Bifidobacterium animalis DN-173 010 on the health-related quality of life and symptoms in irritable bowel syndrome in adults in

(56) References Cited

OTHER PUBLICATIONS primary care: a multicentre, randomized, double-blind, controlled trial", Alimentary Pharmacology & Therapeutics. Apr. 26, 2007, pp. 475-486.

P.J. Whorewll et al, "Efficcy of an Encasulated Probiotic Bifidobacterium infantis 35624 in Woman with Irritable Bowel Syndrome", American Journal of Gastroenterology, 2006, pp. 1581-1590.

S. Duranti et al., "Genomic Characterization and Transcriptional Studies of the Starch-Utilizing Strain Bifidobacterium adolescentis 22L", Applied and Environmental Microbiology, vol. 80 No. 19, Oct. 2014, pp. 6080-6090.

A.M. Zivkovic, "Human milk glycobiome and its impact on the infant gastrointestinal microbiota", PNAS | Mar. 15, 2011 | vol. 108 | suppl. 1 | pp. 4653-4658.

J.S. Frick et al., "Identification of Commensal Bacterial Strains That Modulate Yersinia enterocolitica and Dextran Sodium Sulfate-Induced Inflammatory Responses: Implications for the Development of Probiotics", Infection and Immunity, American Society for Microbiology, vol. 75, No. 7, Jul. 2007, pp. 3490-3497.

T. Pozo-Rubio et al., "Immunostimulatory effect of faecal Bifidobacterium species of breast-fed and formula-fed infants in a peripheral blood mononuclear cell/Caco-2 co-culture system", British Journal of Nutrition, 106, May 31, 2011, p. 1216-1223.

R. Martin et al., "Isolation of Bifidobacteria from Breast Milk and Assessment of the Bifidobacterial Population by PCR-Denaturng Gradient Gel Electrophoresis and Quantitative Real-Time PCR", Applied and Environmental Microbiology, vol. 75, No. 4, Feb. 2009, pp. 965-969.

G.V. Coppa et al., "Oligosaccharides in 4 Different Milk Groups, Bifidobacteria, and Ruminococcus obeum", JPGN, vol. 53, No. 1, Jul. 2011, pp. 80-87.

A. Wittmann et al., "Plasmacytoid Dendritic Cells Are Crucial in Bifidobacterium adolescentis—Mediated Inhibition of Yersinia enterocolitica Infection", PLOS, vol. 8, No. 8, Aug. 2013, pp. 1-10.

P. Wacklin et al., "Secretor Genotype (FUT2 gene) Is Strongly Associated with the Composition of Bifidobacteria in the Human Intestine", PLOS, vol. 6 No. 5, May 2011, pp. 1-10.

C. Hoarau et al., "Supernatant of Bifidobacterium breve induces dendritic cell maturation, activation, and survival through a Toll-like receptor 2 pathway", J Allergy Clin Immunol, vol. 117, No. 3, Mar. 2006, pp. 696-702.

L. Chen, "Therapeutic effects of four strains of probiotics on experimental colitis in mice", World J Gastroenterol Jan. 21, 2009; 15(3): pp. 321-327.

P. Cani et al., "Metabolic endotoxemia initiates obesity and insulin resistance", Diabetes, vol. 56, Jul. 2007, pp. 1761-1772.

\* cited by examiner

SYNTHETIC COMPOSITION FOR PREVENTING OR TREATING CVD

CROSS REFERENCE TO RELATED APPLICATIONS

This is a continuation-in-part of U.S. patent application Ser. No. 15/104,794, filed Jun. 15, 2016, which is a national stage filing in accordance with 35 U.S.C. § 371 of PCT/DK2015/050385, filed Dec. 8, 2015, which claims the benefit of the priority of Denmark Patent Application No. PA 2014 70768, filed Dec. 8, 2014, the contents of each are incorporated herein by reference.

FIELD OF INVENTION

This invention relates to a method and composition for reducing the risk of, preventing, or treating CVD and associated co-morbidities in overweight or obese humans.

BACKGROUND TO THE INVENTION

The increasing trend of obese individuals has become a major health issue over the past several decades and World Health Organization (WHO) has declared obesity as a global epidemic. According to WHO, it was estimated that more than 1.9 billion adults were overweight in 2014, and among them, at least 600 million were obese. This means that worldwide, obesity has more than doubled since 1980 (WHO, fact sheet from January 2015). The rapid increase in obesity over such a short time frame makes a novel genetic cause per se unlikely and strongly favours modified environmental factors over the past 30 years. Such environmental factors include dietary habits, exercise or energy expenditure, and lifestyle. Indeed, there appears to be a strong correlation between Westernization in terms of diet and lifestyle and obesity. A shift from more traditional diets, rich in whole-plant foods like whole-grain cereals, fruits, and vegetables, to modern Western-style diets rich in refined carbohydrates, fat, and red/processed meats and low in fibre and whole-plant foods, is strongly correlated with increased body weight, obesity, and the diseases of obesity (Conterno et al. *Genes Nutr.* 6, 241).

Overweight and obesity is commonly associated with accumulated abdominal visceral fat and can be related to psycho-sociological behavioural disorders. It is often associated with the development of several chronic complications, which increases the risk of developing metabolic diseases such as type 2 diabetes and cardiovascular diseases (CVD) (Boulangé et al. *Genome Medicine* 8, 42 (2016)).

High low-density lipoprotein cholesterol (LDL-C) and triglyceride concentrations and low high-density lipoprotein cholesterol (HDL-C) in the blood is a precursor to hypertension, hyperlipidaemia, and causes the formation and build-up of atherosclerotic plaque in the arteries leading to higher risk of CVD. Cardiovascular risk factors are not only observed in adults, but also obese children and young adults suffer from dyslipidaemia, hypertension, hyperinsulinemia or insulin resistance (Bridger, *Paediatr. Child Health* 14, 177 (2009)).

Cholesterol concentrations within the circulatory pool are products of input from gut absorption and endogenous synthesis relative to clearance through hepatic and extrahepatic tissue pathways. A disruption in any of these mechanisms can alter this balance, which is reflected in plasma cholesterol concentrations and subsequent CVD progression (Matthan et al. *J. Am. Heart Assoc.* 2, e005066 (2013)).

Complex interplay between the gut intestinal microbiota and the diverse human physiological systems are taking plays in the human body, and it has been implicated that an imbalance in this host-microbiota interaction can disrupt the energy homeostasis and lipid metabolism (Zhang et al. *EBioMedicine* 2, 966 (2015); Conterno et al. *Genes Nutr.* 6, 241 (2011)).

Gut microbiota is a specific entity within the body which has its own genome whose gene pool is much more abundant than the one of its host. It has been estimated that the human intestine harbours $10^{13}$ to $10^{r4}$ bacterial cells and the number of bacteria outnumbers the total number of cells in the body by a factor of 10 (Gill et al. *Science* 312, 1355 (2006)). In diet-induced obesity, over-nutrition can alter composition of the gut microbiota, with dietary nutrients influencing the growth of certain species. Diets rich in cholesterol, saturated fats, and simple carbohydrates are associated with a gut microbiota rich in particular organisms belonging to the *Firmicutes* phylum. In line with this, it has been shown that there are marked differences in the gut microbiota between healthy, obese, and type 2 diabetic patients (Bäckhed et al. *PNAS* 101, 15718 (2004), Qin et al. *Nature* 490, 55 (2012)) with fewer Bacteroidetes and more *Firmicutes* in obese than lean people. However, this proportion has shown to change with weight loss leading to increase in the abundance of Bacteroidetes and decrease in the abundance of *Firmicutes* (Ley et al. *Nature* 444, 1022 (2006)). Additionally, specific changes at genus level has been observed with lower number of *bifidobacteria* in obese versus lean and diabetic versus non-diabetic individuals (Schwiertz et al. *Obesity* 18, 190 (2009)).

It would be advantageous to be able to prevent or reduce the damaging consequences of a dysbiotic microbiota in overweight and obesity. Modulation of the microbiota increasing the abundance of beneficial bacteria could be a way to interrupt the processors involved in CVD and hence improve cardiovascular health. Beneficial bacteria such as *bifidobacteria* have shown to ameliorate both metabolic and immunological dysfunctions related to obesity. As an example, *Bifidobacterium pseudocatenulatum* has shown to reduce serum cholesterol, triglyceride and glucose levels and decrease insulin resistance and improve glucose tolerance in obese mice. Additionally, the species can reduce liver steatosis and the number of larger adipocytes in enterocytes of obese mice (Cano et al., *Obesity*, 21, 2310 (2013)).

One mode of action for lowering cholesterol by *bifdobacteria* is the processing of bile salts. Metabolism of cholesterol, a precursor of bile acids, is mediated through the bacteria expressing the enzyme bile salt hydrolase (BSH). Some *bifidobacteria* have high BSH activity promoting deconjugation of bile acids in the gut to secondary amino acid conjugates. When these secondary conjugates are excreted, cholesterol is broken down to replace the processed bile salts. Overall, this process promotes the catabolism of cholesterol, leading to reduced serum levels (Ettinger et al., *Gut Microbes* 5, 719 (2014)). Another mechanism is through bacterial metabolites like short chain fatty acids (SCFA), including acetate, propionate and butyrate. Acetate has shown to be negatively associated with visceral adipose tissue and insulin levels in obese individuals and propionate has shown to reduce lipogenesis and cholesterol synthesis inhibition (Verbeke et al., *Nutrition Research Reviews* 28, 42 (2015)).

Probiotic supplementation could be an approach, however, the addition of a small number of different probiotics to the intestine is unlikely to fully promote a beneficial intestinal microbiota composition with sufficient production of metabolites.

WO 2013/154725 describes that some sialylated and fucosylated HMOs has a positive effect on the growth of certain strains of *bifdobacteria* that are typically found in both infant and adult microbiota.

EP-A-1332759 discloses that oral doses of 2'-FL, 3'-SL, 6'-SL, LNnT and sialic acid promote insulin secretion in type 2 diabetes-model mice.

EP-A-2143341 discloses that a mixture of GOS, sialylated oligosaccharides and N-acylated oligosaccharides reduces triglyceride concentration in liver in model mice.

EP-A-2332552 discloses that 3'-SL and 6'-SL reduce/prevent fat accumulation in the liver and other organs in high-fat diet mice and rats.

WO 2013/057061 discloses a composition for increasing insulin sensitivity and/or reducing insulin resistance. The composition contains long chain polyunsaturated fatty acids, probiotics and a mixture of oligosaccharides containing at least one of lacto-N-neotetraose (LNnT) and lacto-N-tetraose (LNT), at least one N-acetylated oligosaccharide different from LNnT and LNT, at least one sialylated oligosaccharide and at least one neutral oligosaccharide, for use in increasing insulin sensitivity and/or reducing insulin resistance. This composition can also contain 2'-O-fucosyllactose (2'-FL). The composition is particularly adapted for use in infants who were born preterm and/or who experienced IUGR, and in pregnant women suffering from gestational diabetes. It is also stated that the composition can be given to children, adolescents, and adults suffering from insulin resistance and/or type II diabetes. It is stated that the efficacy of the composition can be the result of the synergistic combination of immunity modulator effects triggered by the probiotics and the LC-PUFA through their stimulation with the specific oligosaccharide mixture.

WO 2014/187464 discloses a synthetic mixture of oligosaccharides comprising at least 6 oligosaccharides selected from fucosylated, sialylated, sulfated, GlcNAc- GaINAc- and mannose-containing oligosaccharides, for treating a microbiota of a human, to reduce or eliminate the activity and/or the proportion of a microbe in the microbiota that is associated with the development or maintenance of a cardiovascular disease.

However, there remains a need for effective interventions which are able to prevent or reduce CVD and long-term effects of CVD in CVD patients, especially where the patients are overweight or obese, which are safe, well tolerated and well accepted.

SUMMARY OF THE INVENTION

The present invention provides synthetic compositions comprising one or more HMOs that can be advantageously used to reduce the risk of, prevent or treat CVD or CVD-associated pathologic condition or disease in a human, preferably, in an overweight or obese human individual.

Accordingly, a first aspect of this invention relates to a human milk oligosaccharide or a mixture of two to five human milk oligosaccharides for reducing the propensity of a cardiovascular disease (CVD) and/or a CVD-associated pathological condition or disease in a human, preferably, in an overweight or obese human individual;

second aspect of this invention relates to a human milk oligosaccharide or a mixture of two to five human milk oligosaccharides for preventing development of a cardiovascular disease (CVD) and/or a CVD-associated pathological condition or disease in a human, preferably, in an overweight or obese human individual;

a third aspect of this invention relates to a human milk oligosaccharide or a mixture of two to five human milk oligosaccharides for treating a cardiovascular disease (CVD) and/or a CVD-associated pathological condition or disease in a human, preferably, in an overweight or obese human individual;

a fourth aspect of this invention provides a method for reducing the propensity of a cardiovascular disease (CVD) and/or a CVD-associated pathological condition or disease in a human, preferably, in an overweight or obese human individual, the method comprising administering to the human an effective amount of a human milk oligosaccharide or an effective amount of a mixture of two to five human milk oligosaccharides, or a composition comprising an effective amount of a human milk oligosaccharide or an effective amount of mixture of said two to five human milk oligosaccharides;

a fifth aspect of this invention provides a method for preventing development of a cardiovascular disease (CVD) and/or a CVD-associated pathological condition or disease in a human, preferably, in an overweight or obese human individual, the method comprising administering to the human an effective amount of a human milk oligosaccharide or a mixture of two to five human milk oligosaccharides, or a composition comprising an effective amount of said human milk oligosaccharide, or an effective amount of mixture of said two to five human milk oligosaccharides;

a sixth aspect of this invention provides a method for treating a cardiovascular disease (CVD) and/or a CVD-associated pathological condition or disease in a human, preferably, in an overweight or obese human individual, the method comprising administering to the human an effective amount of a human milk oligosaccharide or a mixture of two to five human milk oligosaccharides, or a composition comprising an effective amount of said human milk oligosaccharide or an effective amount of mixture of said two to five human milk oligosaccharides;

a seventh aspect of this invention provides a method for increasing the abundance of *bifdobacteria* in a human, preferably, in an overweight or obese human having a propensity of, or diagnosed with a cardiovascular disease (CVD), the method comprising administering to the patient one or more HMOs selected from the group consisting of fucosylated HMOs and core HMOs, preferably of a mixture of one or more fucosylated HMOs and one or more core HMOs.

DETAILED DESCRIPTION OF THE INVENTION

It has now been surprisingly found that administration of human milk oligosaccharides (HMOs) to an obese patient, preferentially increases the abundance of *bifdobacteria* in the gastro-intestinal tract, reducing cholesterol and/or hypertension, and through this reduces the risk of CVD and associated co-morbidities. Further, the abundance of members of the *Bifidobacterium adolescentis* phylogenetic group is increased, in particular *B. adolescentis* and/or *B. pseudocatenulatum*.

The increased abundance of *bifdobacteria* leads to production of SCFAs though the fermentation of HMOs and increased activity of BSH. Thus, it has been discovered that HMOs can, by oral or enteral ingestion, increase the production of SCFA and activity of BSH, possibly through modulation of the intestinal microbiota in human. As an outcome, a more beneficial intestinal microbial community can be shaped and maintained, which contributes to attenuation of hypercholesterolemia and hypertension. This can result in reduced risk of, prevention of and/or treatment of, CVD and associated co-morbidities.

Terms and Definitions

The terms "human", "non-infant human" and "non-infant" all mean in the present context a human individual of at least 3 years old. A human can be a child, a teenager, an adult or an elderly, preferably, the human is an individual of at least 3 years old that has an excess of body fat, more preferably, an individual whose excess body fat has accumulated to the extent that it may have a negative effect on health, i.e. an overweight or obese human individual.

Body fat percentage preferably means total mass of body fat divided by total mass of the body.

The term "obese human individual" means that a human individual that has a body mass index (BMI), a measurement obtained by dividing the individual's weight by the square of the individual's height, over 30 kg/m', with the range 25-30 $kg/m^2$ defined as overweight.

Overweight and obesity for children and teens (human individuals aged 3-19 years old) is defined as the following: overweight is defined as a BMI at or above the 85th percentile and below the 95th percentile for children and teens of the same age and sex. Obesity is defined as a BMI at or above the 95th percentile for children and teens of the same age and sex (see: Rolland-Cachera, *Int. J. Pediatr. Obesity* 6, 325 (2011)).

The term "cardiovascular disease (CVD)" refers broadly to any disease of the heart and circulatory system (arteries and veins). Cardiovascular disease generally refers to conditions that involve narrowed or blocked blood vessels that can lead to a heart attack, chest pain (angina) or stroke. Other heart conditions, such as those that affect the heart muscle, valves or rhythm, also are also contemplated as forms of heart disease. Examples of CVD include, but not limited to, coronary artery disease (blockage of blood vessels that serve the heart), acute coronary syndrome (symptoms such as pain, weakness, and tiredness caused by coronary artery disease), angina pectoris (pain resulting from coronary artery disease or other causes), myocardial infarction (heart attack, with damage to heart muscle caused by coronary artery disease), and left ventricular thrombus (blood clot in the left side of the heart that pumps blood into your body).

CVD may be accompanied with health complications (that are interchangeably referred herein as pathologic conditions) or associated diseases, which are also contemplated herein. Some non-limiting examples of relevant contemplated health complications and CVD-associated diseases/ pathologic conditions include heart failure (occurs when the heart cannot adequately pump blood throughout the body; this can cause shortness of breath, dizziness, confusion, and the build-up of fluid in the body, causing swelling), heart attack (occurs when the coronary arteries narrow so much that they cut off blood supply to the heart; the heart cells begin to die as they are deprived of oxygen and symptoms include shortness of breath and severe chest pain that may radiate to the back, jaw, or left arm), stroke (occurs due formation and lodging of blood clots in a blood vessel in the brain and cutting thus off blood flow; stroke symptoms include: numbness on one side of the body, confusion, trouble, speaking, loss of balance or coordination), pulmonary embolism (is similar to a stroke, but the blocked blood vessel is in the lungs instead of the brain; symptoms include shortness of breath, chest pain on breathing, and bluish skin), cardiac arrest (occurs when the heart suddenly stops beating; this will lead to death if not treated immediately), Peripheral Artery Disease (PAD) (occurs due to narrowing in the arteries that supply blood to the arms and legs; the main symptom of PAD is severe leg pain when walking).

The term "patient" means a human who has been diagnosed by a medical practitioner as having a disease or a pathological condition. Both paediatric or adult patient are contemplated. Embodiments of the disease and pathological condition are discussed above. Preferably, the patient is an overweight or obese individual that is having a CVD or a CVD-associated pathological condition or disease.

The term "propensity" in the present context means natural tendency of a human individual to develop later in life a medical condition, such as a disease, in particular a CVD or a CVD-associated pathological condition or disease.

The term "preventing CVD and/or CVD associated pathological condition or disease" in the present context means eliminating or minimising a chance of development of a CVD disease or a pathological condition or disease associated with an CVD. Both primary and secondary prevention are thus contemplated. The primary prevention means preventing a CVD or associated disease or condition before it occurs, and the secondary prevention means preventing additional attacks of a CVD or development of associated condition or disease after the first attack has occurred.

The term "enteral administration" means any conventional form for delivery of a composition to a human that causes the deposition of the composition in the gastrointestinal tract (including the stomach). Methods of enteral administration include feeding through a naso-gastric tube or jujenum tube, oral, sublingual and rectal.

The term "oral administration" means any conventional form for the delivery of a composition to a human through the mouth. Accordingly, oral administration is a form of enteral administration. The term "effective amount" preferably means an amount of a human milk oligosaccharide sufficient to render a desired treatment outcome in a patient. An effective amount can be administered in one or more doses to the patient to achieve the desired treatment outcome.

"Microbiota", "microflora" and "microbiome" preferably mean a community of living microorganisms that typically inhabits a bodily organ or part, particularly the gastrointestinal organs of non-infant humans. The most dominant members of the gastrointestinal microbiota include microorganisms of the phyla of *Firmicutes, Bacteroidetes, Actinobacteria, Proteobacteria, Synergistetes, Verrucomicrobia, Fusobacteria*, and *Euryarchaeota*; at genus level *Bacteroides, Faecalibacterium, Bifidobacterium, Roseburia, Alistipes, Collinsella, Blautia, Coprococcus, Ruminococcus, Eubacterium* and *Dorea*; at species level *Bacteroides uniformis, Alistipes putredinis, Parabacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. The gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

The term "*bifdobacteria*" means a member of the *Bifidobacterium* genus commonly found in the human gastrointestinal tract. Examples of *bifidobacteria* are *Bifidobacterium longum, Bifidobacterium bifidum*, and the members of the phylogenetic *Bifidobacterium adolescentis* group. In non-infant humans, *bifidobacteria* preferably include members of the phylogenetic *Bifidobacterium adolescentis* group.

The term "*Bifidobacterium* of the *Bifidobacterium adolescentis* phylogenetic group" means a bacterium selected from a group consisting of *Bifidobacterium adolescentis, Bifidobacterium angulatum, Bifidobacterium catenulatum, Bifidobacterium pseudocatenulatum, Bifidobacterium kashiwanohense, Bifidobacterium dentum* and *Bifidobacterium stercoris* (Duranti et al. *Appl. Environ. Microbiol.* 79, 336 (2013), Bottacini et al. *Microbial Cell Fact.* 13:S4 (2014)).

The term "relative abundance of *bifidobacteria*" means the abundance of *bifidobacteria* relative to other genus in the microbiota of the gastro-intestinal tract.

The term "human milk oligosaccharide" or "HMO" preferably means a complex carbohydrate consisting of a small number, typically 3-10, of monosaccharide units attached to each other by an interglycosidic linkage that can be found in human breast milk and that can be in acidic or neutral form. More than about 200 different HMO structures are known to exist in human breast milk (Urashima et al.: *Milk Oligosaccharides*, Nova Biomedical Books, New York, 2011). HMOs can be core, fucosylated and sialylated oligosaccharides. Core HMOs are non-fucosylated neutral (that is non-charged) HMOs and consist of Glu, Gal and GlcNAc (thus devoid of Fuc and sialic acid). Examples of core HMOs include lacto-N-tetraose (LNT), lacto-N-neotetraose (LNnT), lacto-N-neohexaose (LNnH), lacto-N-hexaose (LNH) and p-lacto-N-neohexaose (pLNnH). Fucosyl HMOs are fucosylated lactoses or fucosylated core HMOs such as 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose III (LNFP-III), fucosyl-para-lacto-N-neohexaose (F-pLNnH), lacto-N-difucohexaose I (LNDFH-I), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-lacto-N-hexaose III (FLNH-III) and fucosyl-para-lacto-N-neohexaose (F-pLNnH). Sialyl HMOs are sialylated lactoses or sialylated core HMOs such as 3',6-disialyllacto-N-tetraose (DSLNT), 6'-sialyllactose (6'-SL), 3'-sialyllactose (3'-SL), 6'-sialyllacto-N-neotetraose (LST c), 3'-sialyllacto-N-tetraose (LST a) and 6-sialyl-lacto-N-tetraose (LST b). Examples for sialylated and fucosylated HMOs include disialyl-fucosyl-lacto-N-hexaose II (DSFLNH-II), fucosyl-sialyl-lacto-N-neohexaose I (FSLNnH-I), fucosyl-sialyl-lacto-N-hexaose I (FSLNH-I) and 3-fucosyl-3'-sialyllactose (FSL).

The HMOs can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2010/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. With regard to biotechnological methods, WO 01/04341 and WO 2007/101862 describe how to make core human milk oligosaccharides optionally substituted by fucose or sialic acid using genetically modified *E. coli*.

The term "synthetic composition" means a composition which is artificially prepared and preferably means a composition containing at least one compound that is produced ex vivo chemically and/or biologically, e.g. by means of chemical reaction, enzymatic reaction or recombinantly. In some embodiments a synthetic composition of the invention may be, but preferably is not, identical with a naturally occurring composition. The synthetic composition of the invention typically comprises one or more compounds, advantageously HMOs, that are capable of preferentially increasing the abundance of *bifidobacteria*, in particular *Bifidobacterium* of the following species: *Bifidobacterium longum, Bifidobacterium bifidum*, and/or members of the phylogenetic *Bifidobacterium adolescentis* group. In some embodiments, the synthetic composition may comprise one or more compounds or components other than HMOs that may have an effect on *bifidobacteria* of a human subject microbiota in vivo, e.g. non-digestible oligosaccharides or prebiotics. Also in some embodiments, the synthetic compositions may comprise one or more nutritionally or pharmaceutically active components which do not affect adversely the efficacy of the above mentioned compounds. Some non-limiting embodiments of a synthetic composition of the invention are also described below.

Embodiments of the Invention

The invention relates in different embodiments to single HMOs as substantially pure single compounds, i.e. an HMO which grade of purity satisfies the demand of a medical or food authority for marketing, or mixtures of 2 to 5 such substantially pure HMOs, or artificial compositions comprising one to five HMOs. Embodiments of HMOs and compositions comprising thereof are described below.

In particular, different embodiments of the invention relate to HMOs for reducing the propensity of a cardiovascular disease (CVD) in a human individual, preferably in an overweight or obese human individual, preventing development of a cardiovascular disease (CVD) in a human individual, preferably in an overweight or obese human individual, and/or treating a cardiovascular disease (CVD) in a human individual, preferably in an overweight or obese human individual, where the HMOs may be a single HMO or a mixture of two to five of any HMOs suitable for the purpose of the invention. Preferably, the HMO is a fucosylated or a non-fucosylated neutral HMO. More preferably, the invention relates to a mixture of HMOs, the mixture comprising at least a first HMO and at least a second HMO, wherein the first HMO is a fucosylated neutral HMO and the second HMO is a non-fucosylated neutral HMO. In other embodiments the mixture may comprise further a third, a forth and a fifth HMO. Particularly, the mixture of HMOs may contain a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a non-fucosylated HMO selected from the list consisting of LNT, LNnT, LNH, LNnH, pLNH and pLNnH. Preferably, the mixture of HMOs contains a fucosylated HMO selected from the list consisting of 2'-FL, 3-FL and DFL, and a non-fucosylated HMO selected from the list consisting of LNT and LNnT; advantageously the mixture comprises 2'-FL and LNnT and/or LNT. In some embodiments, the mixture of HMOs essentially consists of two neutral HMOs, e.g. a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a non-fucosylated HMO selected from the list consisting of LNT, LNnT, LNH, LNnH, pLNH and pLNnH. Preferably, the mixture essentially consists of a fucosylated HMO selected from the list consisting of 2'-FL, 3-FL and DFL, and a non-fucosylated HMO selected from the list consisting of LNT and LNnT; in one preferred embodiment the mixture essentially consists of 2'-FL and LNnT, in another preferred embodiment the mixture essentially consists of 2'-FL and LNT.

In a preferred embodiment, a mixture of 2'-FL and LNnT may contain the amount of 2'-FL:LNnT form about 1.5:1 to about 4:1.

In other embodiments, the invention relates to a synthetic composition for
  reducing the propensity of a cardiovascular disease (CVD) in a human individual, preferably in an overweight or obese human individual,
  preventing development of a cardiovascular disease (CVD) in a human individual, preferably in an overweight or obese human individual, and/or
  treating a cardiovascular disease (CVD) in a human individual, preferably in an overweight or obese human individual,
which may comprise a single HMO or a mixture of two to five of any HMOs suitable for the purpose of the invention as disclosed above.

The synthetic composition can take any suitable form. For example, the composition can be in the form of a nutritional composition which contains other macronutrients such as proteins, lipids or other carbohydrates. The synthetic composition can also be a pharmaceutical composition.

In other embodiments, the invention relates to a method for
  reducing the propensity of a cardiovascular disease (CVD), or an CVD-associated pathologic condition or disease, in a human, preferably, wherein said human is overweight or obese;
  preventing development of a cardiovascular disease (CVD), or an CVD-associated pathologic condition or disease, in a human, preferably wherein said human is overweight or obese;
  treating a cardiovascular disease (CVD), or an CVD-associated pathologic condition or disease, in a human, preferably, wherein said human is overweight or obese; and/or
  increasing the abundance of *bifidobacteria* in a human having an CVD disease, or an CVD-associated pathologic condition or disease, preferably, wherein said human is overweight or obese,
said method comprising administering to the patient, preferably daily at least 2 g of, a human milk oligosaccharide (HMO) selected from the group consisting of fucosylated HMOs and core HMOs. The HMOs suitable for the purpose of the method are disclosed above.
Nutritional Compositions A nutritional composition can contain sources of protein, lipids and/or digestible carbohydrates and can be in solid, powdered or liquid forms. The composition can be designed to be the sole source of nutrition or a nutritional supplement.

Suitable protein sources include intact, hydrolysed, and partially hydrolysed protein, which can be derived from any suitable source such as milk (e.g., casein, whey), animal (e.g., meat, fish), cereal (e.g., rice, corn), and vegetable (e.g., soy, potato, pea), insect (e.g., locust) and combinations of these sources. Examples of the source of protein include whey protein concentrates, whey protein isolates, whey protein hydrolysates, acid caseins, sodium caseinates, calcium caseinates, potassium caseinates, casein hydrolysates, milk protein concentrates, milk protein isolates, milk protein hydrolysates, non-fat dry milk, condensed skim milk, soy protein concentrates, soy protein isolates, soy protein hydrolysates, pea protein concentrates, pea protein isolates, pea protein hydrolysates, collagen proteins, and combinations of these sources.

The amount of protein is preferably sufficient to provide about 5 to about 30% of the energy of the nutritional composition; for example, about 10% to about 25% of the energy. Within these ranges, the amount of protein can vary depending upon the nutritional needs of the intended individual.

The nutritional compositions can also include free amino acids such as tryptophan, glutamine, tyrosine, methionine, cysteine, taurine, arginine, carnitine, threonine, serine and proline and combinations of these amino acids. Threonine, serine and proline are important amino acids for the production of mucin which aids gut barrier function.

Any suitable source of other carbohydrates can be used. Examples include maltodextrin, hydrolysed or modified starch or corn starch, glucose polymers, corn syrup, corn syrup solids, rice-derived carbohydrates, sucrose, glucose, fructose, lactose, high fructose corn syrup, honey, sugar alcohols (e.g., maltitol, erythritol, sorbitol, etc.), isomaltulose, sucromalt, pullulan, potato starch, slowly-digested carbohydrates, dietary fibres such as oat fibre, soy fibre, gum arabic, sodium carboxymethylcellulose, methylcellulose, guar gum, gellan gum, locust bean gum, konjac flour, hydroxypropyl methylcellulose, tragacanth gum, karaya gum, gum acacia, chitosan, arabinogalactans, glucomannan, xanthan gum, alginate, pectin, low and high methoxy pectin, cereal beta-glucans (i.e., oat beta-glucan, barley beta-glucan), carrageenan and psyllium, Fibersol™, other resistant starches, and combinations of these carbohydrate.

Preferably the carbohydrate source includes low glycemic index carbohydrates having a GI score of 55 or below. Examples of low glycemic index carbohydrates include sucromalt, Fibersol™ (inulin), maltodextrins having a dextrose equivalence (DE) of less than 15, rice syrup having a dextrose equivalence of less than 15, fructooligosaccharides, resistant starches, starches, fruit sourced fibres, vegetable sourced fibres, whole grains, beta-glucans, soy fibres, oat fibres, locust bean gum, konjac flour, hydroxypropyl methylcellulose, gum acacia, chitosan, arabinogalactans, xanthan gum, alginate, low and high methoxy pectin, carrageenan, psyllium, isomaltulose, glycerine and sugar alcohols.

The nutritional compositions can include carbohydrates in an amount sufficient to provide about 30 to about 70% of the energy of the composition, for example about 35 to about 65% of the energy. Within these parameters, the amount of carbohydrate can vary widely.

Suitable lipid sources include coconut oil, fractionated coconut oil, soy oil, corn oil, olive oil, safflower oil, high oleic safflower oil, medium chain triglycerides, sunflower oil, high oleic sunflower oil, palm and palm kernel oils, palm olein, canola oil, marine oils, cottonseed oils and combinations of these oils. Fractionated coconut oils are a suitable source of medium chain triglycerides. The lipids can contain polyunsaturated fatty acids such as n-3 LC-PUFA. The n-3 LC-PUFA can be a C20 or a C22 n-3 fatty acid. Preferably the n-3 LC-PUFA is docosahexanoic acid (DHA, C22:6, n-3). The source of LC-PUFA can be, for example, egg lipids, fungal oil, low EPA fish oil or algal oil.

The nutritional compositions can include lipids in an amount sufficient to provide about 10 to about 50% of energy of the nutritional composition, for example about 15 to about 40% of the energy.

The nutritional composition preferably also includes vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic acid, folk acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 µg/ml to about 10 µg/ml. Lutein can be included in an amount of from about 0.001 µg/ml to about 10 µg/ml, preferably from about 0.044 µg/ml to about 5 µg/ml of lutein. Lycopene can be included in an amount from about 0.001 µg/ml to about 10 µg/ml, preferably about 0.0185 µg/ml to about 5 µg/ml of lycopene. Beta-carotene can comprise from about 0.001 µg/ml to about 10 µg/ml, for example about 0.034 µg/ml to about 5 µg/ml of beta-carotene. The nutritional composition can also include a source of anthocyanins. This can be in the form of a fruit or a fruit extract. Particularly useful fruits and fruit extracts include plum/prune, apple, pear, strawberry, blueberry, raspberry, cherry, and their combinations.

The nutritional composition can also contain various other conventional ingredients such as preservatives, emulsifying agents, thickening agents, buffers, fibres and prebiotics (e.g. fructooligosaccharides, galactooligosaccharides), probiotics (e.g. *B. animalis* subsp. *lactis* BB-12, *B. lactis* HN019, *B. lactis* Bi07, *B. infantis* ATCC 15697, *L. rhamnosus* GG, *L. rhamnosus* HNOOI, *L. acidophilus* LA-5, *L. acidophilus* NCFM, *L. fermentum* CECT5716, *B. longum* BB536, *B. longum* AH1205, *B. longum* AH1206, *B. breve* M-16V, *L. reuteri* ATCC 55730, *L. reuteri* ATCC PTA-6485, *L. reuteri* DSM 17938), antioxidant/anti-inflammatory compounds including tocopherols, caroteinoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can be in the form of a food, soluble powder, a liquid concentrate, or a ready-to-use formulation. The composition can be eaten, drunk or can be fed via a nasogastric. Various flavours, fibres and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra-trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively, the composition can be spray-dried and processed and packaged as a reconstitutable powder.

The nutritional composition can also be in the form of a food such as a nutritional bar, a yoghurt, etc. These forms can be produced using standard technologies and processes.

When the nutritional product is a ready-to-feed nutritional liquid, the total concentration of HMOs in the liquid, by weight of the liquid, is from about 0.0001% to about 2.0%, including from about 0.001% to about 1.5%, including from about 0.01% to about 1.0%. When the nutritional product is a concentrated nutritional liquid, the total concentration of HMOs in the liquid, by weight of the liquid, is from about 0.0002% to about 4.0%, including from about 0.002% to about 3.0%, including from about 0.02% to about 2.0%.

Pharmaceutical Compositions

A pharmaceutical composition of the invention contains an effective amount of HMO or an effective amount of mixture of two to five HMOs, wherein the HMOs are selected from any of described above. The term "effective amount" in the present content means an amount of a single HMO, or a combination of different HMOs that is capable of increasing the abundance of *bifidobacteria* in the gastro-intestinal tract of a human individual of the invention, preferably, relative abundance of members of the *Bifidobacterium adolescentis* phylogenetic group in particular *B. adolescentis* and/or *B. pseudocatenulatum*.

The pharmaceutical composition can further contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical composition can also contain other materials that do not produce an adverse, allergic or otherwise unwanted reaction when administered to humans. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents. If desired, tablet dosages of the anti-infective compositions can be coated by standard aqueous or non-aqueous techniques.

The pharmaceutical compositions can be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions can include binders, lubricants, inert diluents, flavouring agents, and humectants. Orally administered compositions such as tablets can optionally be coated and can be formulated so as to provide sustained, delayed or controlled release of the mixture therein.

The pharmaceutical compositions can also be administered by rectal suppository, aerosol tube, naso-gastric tube or direct infusion into the GI tract or stomach.

The pharmaceutical compositions can also include therapeutic agents most commonly prescribed for heart disease such as:

ACE Inhibitors: ACE inhibitors are a type of medication that dilates (widens) arteries to lower blood pressure and make it easier for the heart to pump blood. They also block some of the harmful actions of the endocrine system that may occur with heart failure;

Aldosterone Inhibitor: Eplerenone (Inspra) and spironolactone (Aldoctone) and eplerenone are potassium-sparing diuretics. They can be prescribed to reduce the swelling and water build-up caused by heart failure. Diuretics cause the kidneys to send unneeded water and salt from the tissues and blood into the urine;

They may improve heart failure symptoms that are still present despite use of other treatments. These drugs protect the heart by blocking a chemical (aldosterone) in the body that causes salt and fluid build-up. This medication is used to treat patients with certain types of severe heart failure;

Angiotensin II Receptor Blocker (ARBs): ARBs are used to decrease blood pressure in people with heart failure. ARBs decrease certain chemicals that narrow the blood vessels so blood can flow more easily through your body. They also decrease certain chemicals that cause salt and fluid build-up in the body;

Beta-Blockers: Beta-blockers block the effects of adrenaline (epinephrine) and thereby improve the heart's ability to perform. They also decrease the production of harmful substances produced by the body in response to heart failure. They cause the heart to beat more slowly and with less force, lowering blood pressure;

Calcium Channel Blockers: Calcium channel blockers are prescribed to treat angina (chest pain) and high blood pressure. Calcium channel blockers affect the movement of calcium in the cells of the heart and blood vessels. As a result, the drugs relax blood vessels and increase the supply of blood and oxygen to the heart, while reducing its workload;

Cholesterol-Lowering Drugs: Cholesterol helps your body build new cells, insulate nerves, and produce hormones. But inflammation may lead to cholesterol build-up in the walls of arteries, increasing the risk of heart attack and stroke;

Digoxin: Digoxin helps an injured or weakened heart to work more efficiently and to send blood through the body. It strengthens the force of the heart muscle's contractions and may improve blood circulation;

Diuretics: Diuretics, commonly known as "water pills," cause the kidneys to get rid of unneeded water and salt from the tissues and bloodstream into the urine. Getting rid of excess fluid makes it easier for your heart to pump. Diuretics are used to treat high blood pressure and reduce the swelling and water build-up caused by various medical problems, including heart failure;

Inotropic Therapy: Inotropic therapy is used to stimulate an injured or weakened heart to pump harder to send blood through the body. It helps the force of the heart muscle's contractions and relaxes constricted blood vessels so blood can flow more smoothly. Inotropic therapy may also speed up the heart's rhythm;

Potassium or Magnesium: Potassium and magnesium are minerals that can be lost because of increased urination when taking diuretics. Low levels in the body can be associated with abnormal heart rhythms. Some patients take them as supplements as directed by their doctor.

Vasodilators: Vasodilators are used to treat heart failure and control high blood pressure by relaxing the blood vessels so blood can flow more easily through the body. Vasodilators are prescribed for patients who cannot take ACE inhibitors.

Warfarin: Warfarin is an anticoagulant medication. "Anti" means "against," and "coagulant" means "causing blood clotting." Therefore, warfarin helps prevent clots from forming in the blood.

The pharmaceutical composition may also contain other compounds such as antibiotics, probiotics, analgesics, and anti-inflammatory agents.

The proper dosage of these compositions for a human can be determined in a conventional manner, based upon factors such as severity of conditions of the human individual, e.g. the individual's blood pressure, immune status, body weight, age, etc.

Administration Dosing

For increasing the levels of the gut hormones GLP-1 and GLP-2 in a person, the amount of human milk oligosaccharide(s) required to be administered to the person will vary depending upon factors such as the risk and condition severity, the age of the person, the form of the composition, and other medications being administered to the person. However, the required amount can be readily set by a medical practitioner and would generally be in the range from about 10 mg to about 20 g per day, in certain embodiments from about 10 mg to about 15 g per day, from about 100 mg to about 10 g per day, in certain embodiments from about 500 mg to about 10 g per day, in certain embodiments from about 1 g to about 7.5 g per day. An appropriate dose can be determined based on several factors, including, for example, the body weight and/or condition of the patient being treated, the severity of the condition, being treated, other ailments and/or diseases of the person, the incidence and/or severity of side effects and the manner of administration. Appropriate dose ranges can be determined by methods known to those skilled in the art. During an initial treatment phase, the dosing can be higher (for example 200 mg to 20 g per day, preferably 500 mg to 15 g per day, more preferably 1 g to 10 g per day, in certain embodiments 2.5 g to 7.5 g per day). During a maintenance phase, the dosing can be reduced (for example, 10 mg to 10 g per day, preferably 100 mg to 7.5 g per day, more preferably 500 mg to 5 g per day, in certain embodiments 1 g to 2.5 g per day).

HMOs of this invention can be co-administered to an individual who is also receiving a standard-of-care medication for obesity or diabetes.

Methods of Treatment

The invention contemplates both prophylactic and therapeutic methods of treatment depending on different embodiments. The term "therapeutic method" means a method comprising treatment of disease or medical disorder by remedial agents and/or, e.g. administering an HMO(s) or a composition of the invention to a CVD patient of the invention to cure the CVD or the associated pathological condition or disease. The term "prophylactic method" means a method comprising a measure taken to fend off a disease or another unwanted consequence of the disease, e.g. administering an HMO or a composition of the invention to a human of the invention to reduce the propensity of or prevent development of CVD or the associated pathological condition or disease in the human.

In particular, the invention relates to the following methods:

a method for reducing the propensity of a cardiovascular disease (CVD), an CVD-associated pathologic condition or disease, in a human, preferably, wherein said human is overweight or obese;

a method for preventing development of a cardiovascular disease (CVD), an CVD-associated pathologic condition or disease, in a human, preferably wherein said human is overweight or obese;

a method for treating a cardiovascular disease (CVD), an CVD-associated pathologic condition or disease, in a human, preferably, wherein said human is overweight or obese; and/or a method for increasing the abundance of *bifidobacteria* in a human having an CVD disease, an CVD-associated pathologic condition or disease, preferably, wherein said human is overweight or obese.

All methods of the invention comprise a step of administering daily to the human at least 2 g of an HMO selected from the group consisting of fucosylated HMOs and core HMOs, preferably, at least 2 g of a mixture of two to five HMOs consisting of one or more fucosylated HMOs and one or more core HMOs.

Preferably, an HMO of the invention is administered to a human in need enteral, e.g. orally. Preferably, invention relates to a method increasing the abundance of a bacterium of the *B. adolescentis* phylogenetic group, especially *Bifidobacterium adolescentis* and/or *B. pseudocatenulatum*.

In any of the methods, one or more HMOs, preferably, one to five HMOs, may be administered as substantially pure compounds (i.e. neat) or diluted, e.g. in form of a solution, power or syrup, or in the form of a synthetic composition, nutritional or pharmaceutical composition, as any of the described above, in one or more unit dosage forms, preferably in a single unit dosage form. Preferably, the HMOs are, or the synthetic, nutritional or pharmaceutical, composition contains, 2'-FL and LNnT, preferably the 2'-FL:LNnT ratio is about 1.5:1 to about 4:1.

The dosage of one or more fucosylated HMOs and one or more core HMOs per administration may vary from about 2 g to about 10 g, preferably from about 3.5 g to about 7.5 g. Typically, the HMOs are administered in a single dosage unit containing from about 2 g to about 10 g, preferably from about 3.5 g to about 7.5 g of one of more fucosylated HMOs and one or more core HMOs. The patient may also additionally receive a dose of one or more species of probiotic bacteria, e.g. *bifidobacteria*.

Typically, the patient is administered a daily dose of at least 2 g of the mixture of one or more fucosylated HMOs and one or more core HMOs for at least 14 days, preferably, for more than 14 days.

EXAMPLES

Examples are now described to further illustrate the invention:

Example 1

Treating High Fat Diet Induced Obesity and Diabetes 10-week-old C57BL/6J mice (100 mice) are housed in groups of five mice per cage, with free water. The mice are divided into 10 groups of 10 mice, one control group and 9 treatment groups. All of the mice are fed a high-fat (HF) diet (60% fat and 20% carbohydrates [kcal/100 g], or an HF diet supplemented with HMO (20 g/kg of diet) for 8 weeks. Food and water intake are recorded twice a week. The 9 treatment groups are each administered one of the following: a) 2'-FL, b) 3-FL, c) 3'-SL, d) 6'-SL, e) LNT, f) LNnT, g) LNFP-I, h) DSLNT and i) a combination of these saccharides. The control group is administered the HF diet only.

Intraperitoneal or oral glucose tolerance tests are performed as follows: 6-h-fasted mice are injected with glucose into the peritoneal cavity (1 g/kg glucose, 20% glucose solution) or by gavage (3 g/kg glucose, 66% glucose solution). Blood glucose is determined with a glucose meter (Roche Diagnostics) on 3.5 µl blood collected from the tip of the tail vein. A total of 20 µl blood is sampled 30 min before and 15 or 30 min after the glucose load to assess plasma insulin concentration.

Plasma triglyceride and cholesterol is measured from blood taken during the treatment period.

To assess intestinal permeability in vivo, the intestinal permeability of 4000 Da fluorescent dextran-FITC (DX-4000-FITC) is measured. Mice are fasted for 6 h before given DX-44-FITC by gavage (500 mg/kg body weight, 125 mg/ml). After 1 h and 4 h, 120 ml of blood is collected from the tip of the tail vein. The blood is centrifuged at 4° C., 12 000 g for 3 min. Plasma is diluted in an equal volume of PBS (pH 7.4) and analysed for DX-4000-FITC concentration with a fluorescence spectrophotometer at an excitation wavelength of 485 nm and emission wavelength of 535 nm. Standard curves are obtained by diluting FITC-dextran in non-treated plasma diluted with PBS (1:3 v/v).

Mice are anaesthetised (ketamine/xylazine, intraperineally, 100 and 10 mg/kg, respectively) after a 5 h period of fasting, blood samples and tissues are harvested for further analysis. Mice are killed by cervical dislocation. Liver, caecum (full and empty), and adipose tissues (mesenteric and corresponding lymph nodes, epididymal, subcutaneous and visceral) are precisely dissected, weighed and stored at −80° C., for further analysis.

Total and active GLP-1 are measured from blood with ELISA (Millipore, Molsheim, France).

To assess the microbiota profile, the caecal contents collected post mortem from mice are stored at −80° C. DNA is isolated from the caecal content samples using QIAamp DNA Stool Mini Kit. The DNA concentration of extracts is measured using NanoDrop. Aliquots of 100 ng of extracted DNA are subjected to PCR using the 16S rDNA universal heteroduplex analysis (HDA) primers HDA1-GC 50-CGCCCGGGGCGCGCCCCGGGCGGG-GCGGGGGCACGGGGGGACTCCTACGG-GAGGCAGCAGT-30 and HDA2 50-TTACCGCGGCTGCTGGCA-30 (both primers are disclosed in Walter et al. *Appl. Environ. Microbiol.* 66, 297 (2000)) at 56° C. for strand annealing. Initial denaturation at 94° C. for 4 min is followed by thirty cycles of 30 s at 94° C., 30 s at 56° C. and 1 min at 72° C. The quality of PCR products is verified by agarose gel electrophoresis. Amplified 16S rDNA fragments are separated by denaturing gradient gel electrophoresis (DGGE) using an INGENYphorU system equipped with 6% polyacrylamide gels with a denaturant in the range of 30-55%, where 100% denaturant is equivalent to 7M-urea and 40% formamide. Electrophoresis is carried out at 130 V for 4-5 hours at 60° C. Polyacrylamide gels are stained with GelRede nucleic acid stain for 45 min, destained in ultrapure water and viewed under UV light. Bands of interest are excised from gels and lysed in ultrapure water. Extracted DNA is re-amplified using the same primers and PCR conditions. To purify the bacterial DNA, PCR products are reloaded on a denaturant gradient gel followed by excision and lysis of selected bands. DNA samples recovered from lysed bands of the second DGGE are re-amplified by PCR before purification using the QIAquick PCR Purification Kit and sequenced. Species identification is done using the Ribosomal Microbiome Database Project Classifier tool. Because of the limited sensitivity of DGGE to quantify microbial diversity, the microbial composition of DNA samples is also analysed using high-throughput sequencing. The V5-V6 region of 16S rRNA from caecal content DNA samples is amplified using the primers 784F 50-AGGATTAGATACCCT-GGTA-30 and 1061R 50-CRRCACGAGCTGACGAC-30 3640 (both primers are disclosed in Andersson et al. *PloS ONE* 3, e2836 (2008)). Amplicons are pyrosequenced using a Roche 454 GS-FLX system. Sequences of at least 240 nucleotides and containing no more than two undetermined bases are retained for taxonomic assignment. The QIIME software is used for chimera check and the Greengenes database is used for classification. Bacterial diversity is determined at the phylum, family and genus levels.

The results show that HMOs are able to change the intestinal microbiota by increasing the abundance of *bifidobacteria*. Additionally, HMO supplementation reduces cholesterol, body weight, fat accumulation and glucose tolerance.

Example 2

Human Trial in Overweight and Obese Children

A total of 60 male and female patients, enrolled to a childhood obesity treatment program, are recruited to participate in the study. Patients are randomized into three groups, each of 20 patients, with 2 groups receiving different investigational products and one group receiving a placebo product for 8 weeks. The investigational products contain 4.5 grams of either 2'-FL alone or a combination of 2'-FL and LNnT while the placebo product contains 4.5 grams glucose. All products are in powder form in a unit dosage container.

The patients are eligible to participate if: they are between 5 and 10 years of age, have a BMI SDS of ≥2.0 and are enrolled in the childhood obesity treatment program at the Children's Obesity Clinic. All recruited patients and their representatives are able and willing to understand and comply with the study procedures. Patients are excluded if: they have participated in a clinical study one month prior to the screening visit and throughout the study; have any gastrointestinal disease(s) that may cause symptoms or may interfere with the trial outcome; have other severe disease(s) such as malignancy, kidney disease or neurological disease; have psychiatric disease; have used highly dosed probiotic supplements (yoghurt allowed) 3 months prior to screening and throughout the study; have consumed antibiotic drugs 3 months prior to screening and throughout the study; and consume on a regular basis medication that might interfere with symptom evaluation 2 weeks prior to screening and throughout the study.

At the initial visit (screening) patients and their representatives are given both oral and written information about the study; the children are asked for informed assent and their representatives to sign an informed consent form.

Eligibility criteria are checked and for children who are enrolled to the study, medical history and concomitant medication are registered. A physical examination is done and pubertal staging is determined. Blood pressure, pulse rate, height and bodyweight are measured, and body composition is determined by a DXA (dual energy x-ray absorptiometry)-scan and bioimpedance. BMI SDS is calculated, waist and hip circumferences measured and food intake registered. Fasting blood samples are collected for safety and biomarker studies and for biobanking.

The serum from the blood samples is transferred to cryotubes and stored at −80° C. The following biomarkers are measured; Lipopolysaccharides (LPS), hsCRP, free fatty acids, total cholesterol, HDL, LDL, HbA1c, glucose, insulin, triglycerides, TNF-α, IL-Iβ, IL-6, IL-8, IL-10, GLP-1, GLP-2, Adiponectin, and Zonulin.

Equipment for collecting faecal samples is distributed. The faecal samples are stored at −80° C. until analysis. SCFA and Microbiological analysis is performed on the faecal samples.

The Gastrointestinal Symptom Rating Scale (GSRS) questionnaire is completed on site by the participating child's representative(s), and the Bristol Stool Form Scales (BSFS) is distributed to the participant's representative(s) with instructions to assess the stool consistency during the study and at each faecal sampling point using the BSFS.

At the second visit (randomization), patients and their representatives are asked about adverse events, faecal samples are collected and equipment for collection of new samples is distributed. BSFS is collected and new BSFS is distributed. Study products are distributed together with a compliance form (diary). Patients and their representatives are reminded to follow the healthy dietary habits.

The study runs for 8 weeks with the patients consuming either a placebo or one of two investigational products daily. Patients are instructed to consume the products in the morning with breakfast. Compliance is monitored via a compliance form (diary) to be filled in daily.

Four weeks after commencement there is an intermediate check. Patients and their representatives are asked about adverse events and any changes in the patient's usual medication. Faecal samples are collected and equipment for collection of new samples is distributed. Blood pressure, pulse rate, waist and hip circumference, height and bodyweight are measured and BMI SDS calculated. The GSRS is completed on site by the participating child's representative. The BSFS is collected and new BSFS is distributed to the participant's representative(s) with instructions to assess the stool consistency at each faecal sampling point using the BSFS. Patients and their representatives are reminded to follow the healthy dietary habits.

At the end of intervention (8 weeks), each patient has a visit with the medical team. Patients and their representatives are asked about adverse events and any changes in the patient's usual medication. Study products and compliance forms are collected to check compliance. BSFS and faecal samples are collected and equipment for collection of new samples is distributed. A physical examination is done and pubertal staging is determined. Blood pressure, pulse rate, height and bodyweight are measured, and body composition is determined by a DXA (dual energy x-ray absorptiometry)-scan and bioimpedance. BMI SDS is calculated, waist and hip circumferences measured and food intake registered. Fasting blood samples are collected for safety and biomarker studies and for biobanking, and equipment for collecting faecal samples is distributed. The GSRS questionnaire is completed on site by the participating child's representative(s).

To examine potential long term effects of the intervention, an un-blinded follow-up period follows with a visit 8 weeks after end of intervention. A physical examination is done and pubertal staging is determined. Blood pressure, pulse rate, height and bodyweight are measured, and body composition is determined by a DXA (dual energy x-ray absorptiometry)-scan and bioimpedance. BMI SDS is calculated, waist and hip circumferences measured and food intake registered. Fasting blood samples are collected for safety and biomarker studies and for biobanking. Faecal samples are collected.

The results show that oral ingestion of HMOs modulate the intestinal microbiota, and specifically stimulate the growth of bifidobacteria, particular species belonging to the B. adolescentis phylogenetic group, and change the SCFA profile. The blood biomarker analysis indicated that the patients given the investigational products have a lipid profile with lower triglyceride levels and higher high-density lipoprotein cholesterol. Additionally, the blood pressure and body composition is decreased. The abundance of bifdobacteria correlates negatively with the level of low-density lipoprotein cholesterol and positively with the level of high-density lipoprotein cholesterol. Collectively, HMOs are able to increase bifdobacteria and change the intestinal environment, and by this, improve the lipid profile, hypertension and body composition, all incidence reducing the risk of CVD.

Example 3

Nutritional Composition

A ready to feed nutritional composition is prepared from water, maltodextrin, milk protein concentrate, Sucromalt, glycerine, cocoa powder, soy protein isolate, fructose, high oleic safflower oil, soy oil, canola oil, plant sterol esters, HMOs, soy lecithin, magnesium chloride, calcium phosphate, carrageenan, sodium ascorbate, potassium citrate, sodium phosphate, calcium citrate, choline chloride, potassium chloride, sodium citrate, magnesium oxide, taurine, L-carnitine, alpha-tocopheryl acetate, zinc sulphate, ferrous sulphate, niacinamide, calcium pantothenate, vitamin A palmitate, citric acid, manganese sulphate, pyridoxine hydrochloride, vitamin D3, copper sulphate, thiamine mononitrate, riboflavin, beta carotene, folic acid, biotin, potassium iodide, chromium chloride, sodium selenate, sodium molybdate, phytonadione, vitamin B12.

The composition has an energy density of 0.8 kcal/ml with an energy distribution (% of kcal) as follows: protein: 20%, carbohydrate: 48%, fat: 32%.

Example 4

Tablet Composition

A tablet is prepared from HMO, hydroxypropyl methylcellulose, sodium alginate, gum, microcrystalline cellulose, colloidal silicon dioxide, and magnesium stearate. All raw materials except the magnesium stearate are placed into a high shear granulator and premixed. Water is sprayed onto the premix while continuing to mix at 300 rpm. The granulate is transferred to a fluidised bed drier and dried at 75° C. The dried powder is sieved and sized using a mill. The resulting powder is then lubricated with magnesium stearate and pressed into tablets. The tablets each contain 325 mg of HMO. The tablets each have a weight of 750 mg.

Example 5

Capsule Composition

A capsule is prepared by filling about 1 g of HMO into a 000 gelatine capsule using a filing machine. The capsules are then closed. The HMO are in free flowing, powder form.

The invention claimed is:
1. A method for reducing a risk of heart failure in a non-infant human, the method comprising:
increasing the relative abundance of Bifidobacterium adolescentis in the microbiota of the non-infant human by administering daily to the non-infant human about 2 g to about 10 g of a mixture consisting essentially of two to five synthetic neutral human milk oligosaccharides (HMOs),
wherein at least one of the synthetic neutral HMOs is a fucosylated HMO selected from 2'-fucosyllactose (2'-FL), 3-fucosyllactose (3-FL) and difucosyllactose (DFL), and
wherein at least one of the synthetic neutral HMOs is a non-fucosylated HMO selected from lacto-N-tetraose (LNT) and lacto-N-neotetraose (LNnT).
2. The method of claim 1, in which from about 3.5 g to about 7.5 g of the mixture is administered daily.
3. The method of claim 1, in which the mixture consists essentially of 2'-FL and LNnT.
4. The method of claim 3, wherein the 2'-FL:LNnT ratio is about 1.5:1 to about 4:1.
5. The method of claim 1, in which the HMOs of the mixture are administered as undiluted compounds or in the form of a synthetic composition, in one or more unit dosage forms.
6. The method of claim 1, in which the mixture is enterally administered.
7. The method of claim 1, in which the non-infant human is administered daily the 2 g to about 10 g of the mixture for at least 14 days.
8. The method of claim 1, in which the non-infant human is overweight or obese.
9. A method for reducing a risk of developing a cardiovascular disease selected from stroke, pulmonary embolism, and peripheral artery disease (PAD), in a patient that is an adult human, the method comprising:
increasing the relative abundance of Bifidobacterium adolescentis in the microbiota of the adult human patient by administering a mixture consisting essentially of two to five neutral human milk oligosaccharides (HMOs), wherein at least one of the neutral HMOs is a fucosylated HMO selected from 2'-fucosyllactose (2'-FL), 3-fucosyllactose (3-FL) and difucosyllactose (DFL), and wherein at least one of the neutral HMOs is a non-fucosylated HMO selected from lacto-N-tetraose (LNT) and lacto-N-neotetraose (LNnT).
10. The method of claim 9, further comprising increasing production of short chain fatty acids in the patient.
11. The method of claim 9, wherein increasing the relative abundance of the Bifidobacterium adolescentis is relative to an abundance of one or more microorganisms present in the microbiota of the patient selected from the phylum Firmicutes and the phylum Proteobacteria phyla.
12. The method of claim 9, wherein administering the mixture comprises orally administering the mixture daily.

13. The method of claim 9, in which the mixture consists essentially of 2'-FL and LNT.

14. A method of treating a cardiovascular disease (CVD) in an obese human patient at least five years of age having CVD, the method comprising:
increasing the relative abundance of *Bifidobacterium adolescentis* in the microbiota of the obese human patient by administering a mixture consisting essentially of two to five synthetic neutral HMOs,
wherein at least one of the synthetic neutral HMOs is a fucosylated HMO selected from 2'-fucosyllactose (2'-FL), 3-fucosyllactose (3-FL), difucosyllactose (DFL), and lacto-N-fucopentaose I (LNFP-I), and
wherein at least one of the synthetic neutral HMOs is a non-fucosylated HMO selected from lacto-N-tetraose (LNT) and lacto-N-neotetraose (LNnT).

15. The method of claim 14, wherein administering the mixture increases production of short chain fatty acids in the patient.

\* \* \* \* \*